United States Patent [19]
Rohler et al.

[11] Patent Number: 6,130,958
[45] Date of Patent: Oct. 10, 2000

[54] METHOD FOR RECONSTRUCTING THE IMAGE OF AN OBJECT SCANNED WITH A LASER IMAGING APPARATUS

[75] Inventors: David P. Rohler; Sastry L. A. Kasibhatla, both of University Heights, Ohio; Steven Ross, Boca Raton, Fla.

[73] Assignee: Imaging Diagnostic Systems, Inc., Plantation, Fla.

[21] Appl. No.: 08/979,624

[22] Filed: Nov. 28, 1997

Related U.S. Application Data

[60] Provisional application No. 60/032,594, Nov. 29, 1996.

[51] Int. Cl.[7] .............................. G06K 9/00; G03H 1/02; G01J 5/02; A61B 6/04
[52] U.S. Cl. ............................ 382/131; 382/255; 359/27; 359/32; 250/339.06; 378/37; 600/425
[58] Field of Search ............................ 382/128, 131, 382/255; 359/32, 27; 250/336.1, 339.06; 378/37; 600/425, 473, 476

[56] References Cited

U.S. PATENT DOCUMENTS

| | | | |
|---|---|---|---|
| 3,863,154 | 1/1975 | Marwell et al. | 368/114 |
| 4,360,885 | 11/1982 | Edgar | 382/131 |
| 4,499,430 | 2/1985 | Fujii | 330/279 |
| 4,554,460 | 11/1985 | Klein | 250/208.2 |
| 4,767,928 | 8/1988 | Nelson et al. | 250/341.7 |
| 4,945,239 | 7/1990 | Wist et al. | 250/358.1 |
| 5,008,822 | 4/1991 | Brunnett et al. | 600/425 |
| 5,148,022 | 9/1992 | Kawaguchi et al. | 250/339.06 |
| 5,231,464 | 7/1993 | Ichimura et al. | 356/345 |
| 5,293,312 | 3/1994 | Waggener | 378/14 |
| 5,371,368 | 12/1994 | Alfano et al. | 250/341.1 |
| 5,381,224 | 1/1995 | Dixon et al. | 356/72 |
| 5,386,819 | 2/1995 | Kaneko et al. | 600/177 |
| 5,408,093 | 4/1995 | Ito et al. | 250/227.26 |
| 5,471,049 | 11/1995 | Cain | 250/208.2 |
| 5,477,051 | 12/1995 | Tsuchiya | 250/341.1 |
| 5,572,118 | 11/1996 | Lewis | 324/123 R |
| 5,588,032 | 12/1996 | Johnson et al. | 378/8 |
| 5,640,436 | 6/1997 | Kawai et al. | 378/4 |
| 5,672,875 | 9/1997 | Block et al. | 250/343 |
| 5,692,511 | 12/1997 | Grable | 600/425 |
| 5,708,414 | 1/1998 | Peltier et al. | 340/506 |
| 5,717,608 | 2/1998 | Jensen | 702/130 |
| 5,719,398 | 2/1998 | Colak | 250/341.1 |
| 5,739,539 | 4/1998 | Wang et al. | 250/363.04 |
| 5,815,410 | 9/1998 | Heinke et al. | 702/135 |
| 5,854,851 | 12/1998 | Bamberger et al. | 382/132 |
| 5,880,827 | 3/1999 | Heinke | 356/224 |

OTHER PUBLICATIONS

First Demonstration of Laser Computed Tomography of Human Tooth by Coherent Detection Imaging, Deveraj et al; IEEE Paper, ISSN: 0013–5194, vol. 31, Issue 11, pp. 874–876, May 25, 1995.

Three–Dimensional Imaging of Laser–Imploded Targets using X–ray Computed Tomography Techniques, Chen et al; IEEE Conference on Nuclear Science Symposium; ISBN: 0–7803–3534–1, vol. 1, pp. 283–286, Nov. 2, 1996.

Microwave Tomography: two–Dimensional System for Biological Imaging, Semenov et al; IEEE Transaction on Biomedical Engineering; ISSN: 0018–9294, vol. 43, Issue 9, pp. 869–877, Sep. 1996.

Chrono–Coherent Imaging for Medicine, Spears et al; IEEE Transaction on Biomedical Engineering; ISSN: 0018–9294, vol. 36, Issue 12, pp. 1210–1221, Dec. 1989.

S.B. Colak et al., "Tomographic image reconstruction from optical projections in light–diffusing media", Jan. 1, 1997, vol. 36, No. 1, pp. 180–213.

*Primary Examiner*—Amelia Au
*Assistant Examiner*—Mehrdad Dastouri
*Attorney, Agent, or Firm*—Shlesinger, Arkwright & Garvey LLP

[57] ABSTRACT

A method for reconstructing an image of a scanned object comprises the steps of collecting object data by scanning the object with a laser beam and detecting the light passing through the object; collecting perimeter data of the object during the scanning step; transforming the object data to parallel ray geometry; correcting the projection data using the perimeter data; and backprojecting the data in image space.

33 Claims, 5 Drawing Sheets

METHOD FOR RECONSTRUCTING THE IMAGE OF AN OBJECT SCANNED WITH A LASER IMAGING APPARATUS

RELATED APPLICATIONS

This application is a related to provisional application Ser. No. 60/032,594, filed on Nov. 29, 1996, which is hereby incorporated by reference and whose priority is hereby claimed.

This application is also related to application Ser. No. 08/484,904, filed Jun. 7, 1995, now U.S. Pat. No. 5,692,511, issued on Dec. 2, 1997, which is hereby incorporated by reference.

FIELD OF THE INVENTION

The present invention relates generally to a diagnostic medical imaging apparatus that employs a near-infrared laser as a radiation source and more particularly to a method for reconstructing an image of a scanned object using perimeter data obtained during the scanning process to correct for optical distortions of the object data.

BACKGROUND OF THE INVENTION

Cancer of the breast is a major cause of death among the American female population. Effective treatment of this disease is most readily accomplished following early detection of malignant tumors. Major efforts are presently underway to provide mass screening of the population for symptoms of breast tumors. Such screening efforts will require sophisticated, automated equipment to reliably accomplish the detection process.

The x-ray absorption density resolution of present photographic x-ray methods is insufficient to provide reliable early detection of malignant tumors. Research has indicated that the probability of metastasis increases sharply for breast tumors over 1 cm in size. Tumors of this size rarely produce sufficient contrast in a mammogram to be detectable. To produce detectable contrast in photographic mammogram 2–3 cm dimensions are required. Calcium deposits used for inferential detection of tumors in conventional mammography also appear to be associated with tumors of large size. For these reasons, photographic mammography has been relatively ineffective in the detection of this condition.

Most mammographic apparatus in use today in clinics and hospitals require breast compression techniques which are uncomfortable at best and in many cases painful to the patient. In addition, x-rays constitute ionizing radiation which injects a further risk factor into the use of mammographic techniques as most universally employed.

Ultrasound has also been suggested as in U.S. Pat. No. 4,075,883, which requires that the breast be immersed in a fluid-filled scanning chamber. U.S. Pat. No. 3,973,126 also requires that the breast be immersed in a fluid-filled chamber for an x-ray scanning technique.

In recent times, the use of light and more specifically laser light to non-invasively peer inside the body to reveal the interior structure has been investigated. This technique is called optical imaging. Optical imaging and spectroscopy are key components of optical tomography. Rapid progress over the past decade have brought optical tomography to the brink of clinical usefulness. Optical wavelength photons do not penetrate in vivo tissue in a straight line as do x-ray photons. This phenomena causes the light photons to scatter inside the tissue before the photons emerge out of the scanned sample.

Because x-ray photons propagation is essentially straight-line, relatively straight forward techniques based on the Radon transform have been devised to produce computed tomography images through use of computer algorithms. Multiple measurements are made through 360° around the scanned object. These measurements, known as projections, are used to back-project the data to create an image representative of the interior of the scanned object.

In optical tomography, mathematical formulas and projection techniques have been devised to perform a reconstruction function somewhat similar to x-ray tomography. However, because light photon propagation is not a straight line, techniques to produce cross-section images are mathematically intensive and invariably require establishing the boundary of the scanned object. Boundary determination is important because it serves as the basis for reconstruction techniques to produce interior structure details. Algorithms to date do not use any form of direct measurement techniques to establish the boundary of the scanned object.

OBJECTS AND SUMMARY OF THE INVENTION

It is an object of the present invention to provide a reconstructed image of a scanned object using a laser scanning apparatus with minimum data distortion.

It is another object of the present invention to provide a reconstructed image of a scanned object with reduced amount of time by using perimeter data obtained during the scanning process.

It is still another object of the present invention to provide a reconstructed image of a scanned object using perimeter data obtained during the scanning process to correct for optical distortions to the raw data.

It is another object of the present invention to provide a reconstructed image of a scanned object using perimeter data obtained during the scanning process to locate each pixel within the image data, which location is then used to access look-up tables to correct each pixel for optical distortions.

In summary, the present invention provides a method for reconstructing an image of a scanned object, comprising the steps of collecting object data by scanning the object with a laser beam and detecting the light passing through the object; collecting perimeter data of the object during the scanning step; transforming the object data to parallel ray geometry; correcting the projection data using the perimeter data; and backprojecting the data in image space.

These and other objects of the present invention will become apparent from the following detailed description.

DETAILED DESCRIPTION OF THE INVENTION

Figure 1:
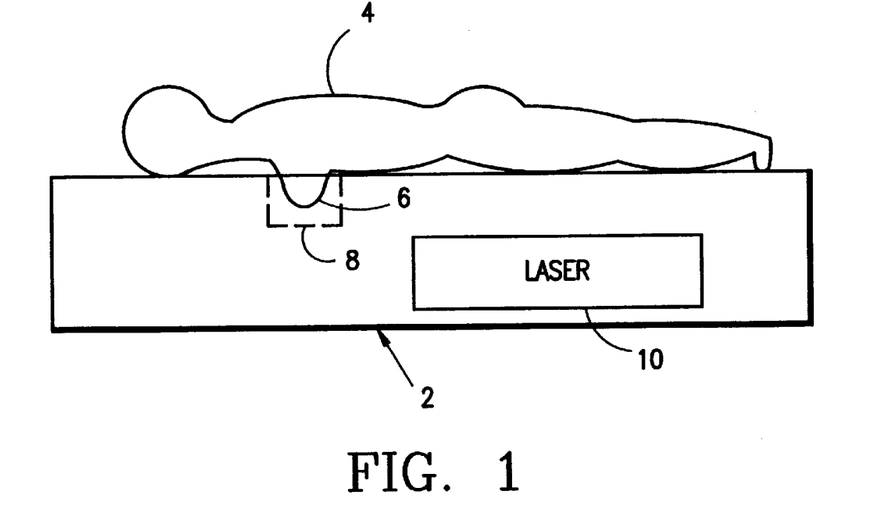
FIG. 1 is a schematic side elevational view of a scanning apparatus including a scanning chamber made in accordance with the present invention, showing a patient positioned on a support platform with her breast pendent within the scanning chamber for optical tomographic study.

A scanning apparatus 2, such as that described in copending application Ser. No. 08/484,904, filed Jun. 7, 1995, is schematically disclosed in FIG. 1. A patient 4 is positioned prone on a top surface of the apparatus 2 with her breast 6 pendent within a scanning chamber 8. A laser beam from a laser source 10 is operably associated with the scanning chamber 8 to illuminate the breast 6.

Figure 2:
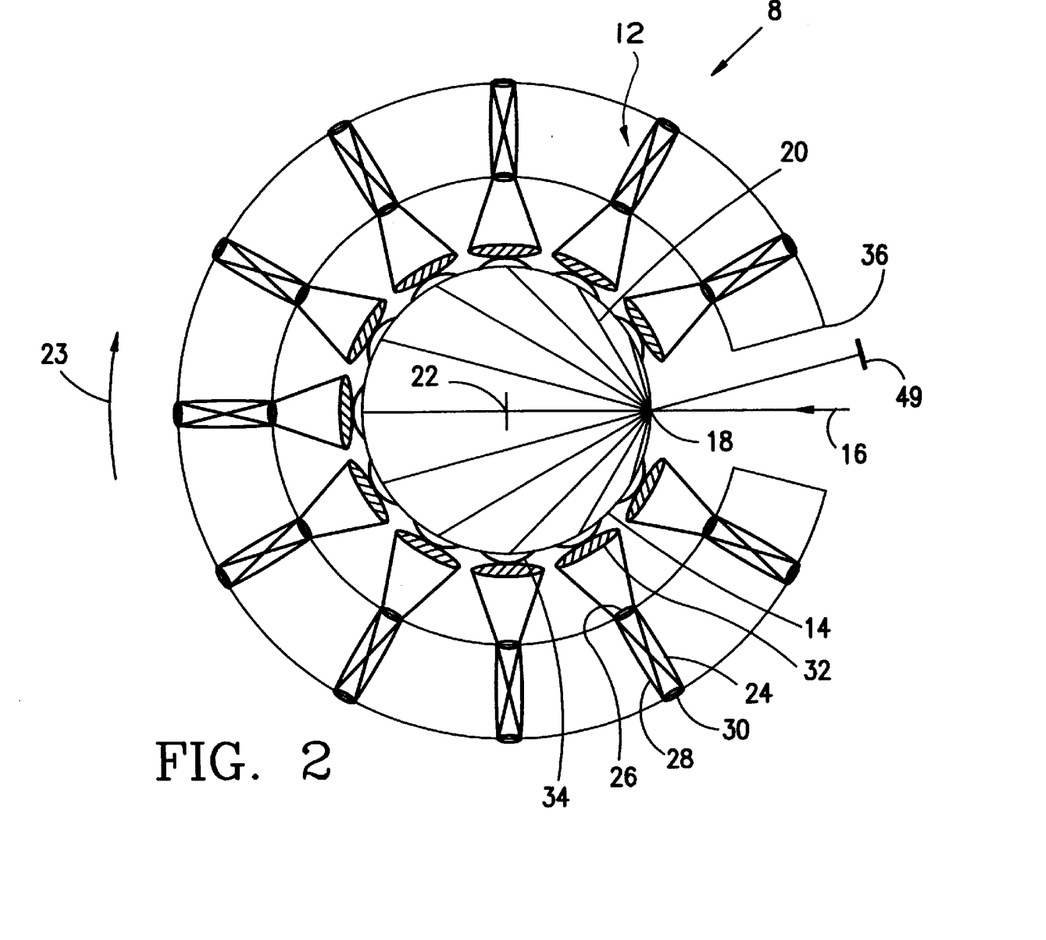
FIG. 2 is a schematic plan view of the scanning chamber of FIG. 1, showing the restricted field of views of the respective detectors and the optical chord lengths of the laser beam through the object.

The scanning chamber 8 is shown schematically in plan view in FIG. 2. The scanning chamber includes a plurality of detector assemblies 12 disposed in an arc to define an opening in which an object 14 to be scanned, such as the breast, is positioned. A laser beam 16 impinges the object at point 18. Light exiting from the object 18, such as the rays 20 is picked up by the respective detector assembly 12, which is then used to provide an image of the scanned object. The rays 20 are represented as chords originating from the point of entry 18 of the laser beam 16 and exiting at various points on the perimeter of the scanned object. The detector assemblies 12 are digitally orbited around the object 14 about an orbit center 22 at equal angular increments for a total angular displacement of 360°. The object is illuminated with the laser beam 16 at each angular position in the orbit 23 and light emerging from the object depicted by the chords 20 on the perimeter of the scanned object, at one instant in time or in a period of time acquired simultaneously, is picked up by the respective detector assemblies 12. Each detector assembly has its longitudinal axis directed toward the orbit center 22. The detector assemblies 12 are secured to a support 36, which is orbited in orbit 23 around the object 14 being scanned. After each complete orbit, the array of detector assemblies 12 and the laser beam 16 are moved vertically to a new position to scan a different slice plane of the object. This is repeated until all the slice planes of the object has been scanned.

Each detector assembly 12 includes an opaque housing 24 with an open front end 26 and a rear end 28 in which a detector 30 is disposed. The inside surface of the housing 24 can be tubular, round, square or other cross-sectional shape. The housing 24 is designed to restrict the field of view of its respective detector 30, such that each detector is only looking at its own small area of the scanned object. The field of view of each detector assembly 12 is schematically indicated at 32. A patch or surface seen on the scanned object by the respective detector assembly is schematically indicated at 34.

The field of view 32 and the respective patch of surface 34 are configured such that adjacent patches of surface do not overlap each other. In this way, each detector assembly is uniquely assigned to a patch of surface at each angular position of the orbit so that light coming from one patch of surface could only be detected by the respective detector whose field of view covers that particular patch of surface. Each detector 30 is active to detect any light emerging from its respective patch of surface, since the light beam 16 can course through the object in any paths, such as those depicted by the chords 20. Each housing is further described in a copending application Ser. No. 08/963,760, filed Nov 4, 1997, claiming priority based on provisional application Ser. No. 60/032,591, filed Nov. 29, 1996, both of which are hereby incorporated by reference.

Figure 3:
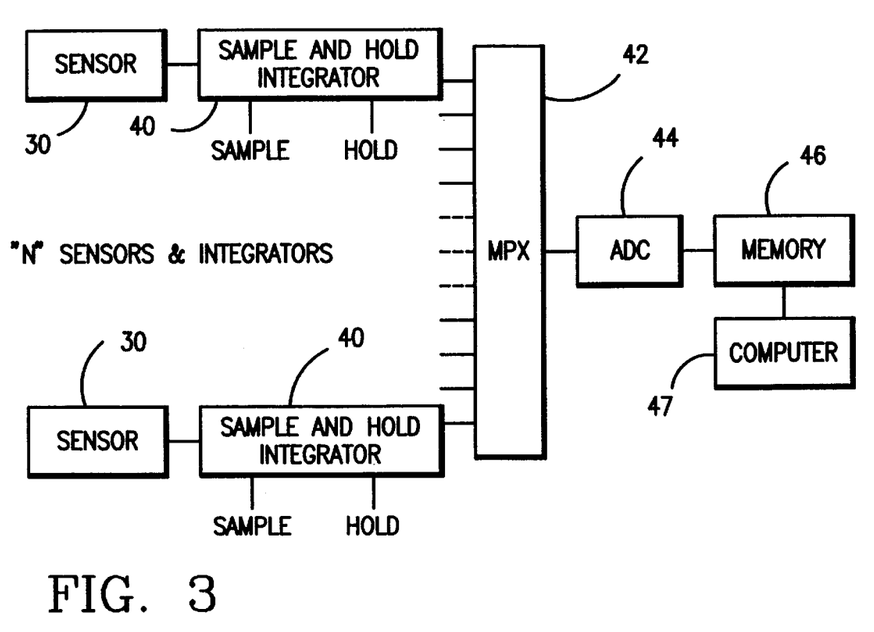
FIG. 3 is a schematic block diagram of a circuit for collecting data from each detector.

Each detector or sensor 30 is operably connected to its respective sample and hold integrator 40, as best shown in FIG. 3. A multiplexer 42 is used to connect the respective integrator outputs to an analog-to-digital converter 44. The digitized individual detector or sensor response is stored in memory 46 for later use in image reconstruction by a computer 47. The circuit allows for simultaneous acquisition of data from all the detectors 30 at each angular position in the orbit of the scanning chamber 8. The sample and hold integrator 40 is further described in a copending application Ser. No. 08/979,328, filed on Nov. 26, 1997, claiming priority based on provisional application Ser. No. 60/032,590, filed on Nov. 29, 1996, both of which are hereby incorporated by reference.

Perimeter data of the object being scanned is obtained at each angular position in the orbit of the scanning chamber 8. Several methods are disclosed in copending applications Ser. No. 08/965,148, entitled, "Apparatus for Determining the Perimeter of the Surface of an Object Being Scanned," filed on Nov. 6, 1997, claiming priority from provisional application Ser. No. 60/029,897 filed Nov. 8, 1996 and Ser. No. 08/965,149 entitled, "Device for Determining the Perimeter of the Surface of an Object Being Scanned and for Limiting Reflection From the Object Surface," filed on Nov. 6, 1997, claiming priority from provisional application Ser. No. 60/029,898 filed Nov. 8, 1996, all of which are hereby incorporated by reference. One method is to use a sensor array 49 disposed on the same side as the laser beam 16, as best shown in FIG. 2. The laser beam 16 impinges on the scanned object through the center of the orbit. Bright spot is produced at point 18. At each distance from the orbit center, a specific element in the sensor array 49 will detect the bright spot. As the laser beam 16 and the rest of the scanner are orbited around the scanned object about the center, the output signal of the sensor array 49 will be in direct relationship to the perimeter of the scanned object. By acquiring data using one or more known diameters scanned objects, the level of the sensor signal can be calibrated with respect to the scanned object diameters. After calibration, the sensor signal can be electronically decoded to plot the coordinates for the perimeter of the scanned object as the scanner is orbited around the scanned object.

It is advantageous to obtain the perimeter data during data collection of each slice to minimize error due to shifting of the object between slice positions. Perimeter data and the corresponding detector data are used together to reconstruct the image of the object. Perimeter data consist of distances from the center of orbit at each angular position of the orbit.

Figure 4:
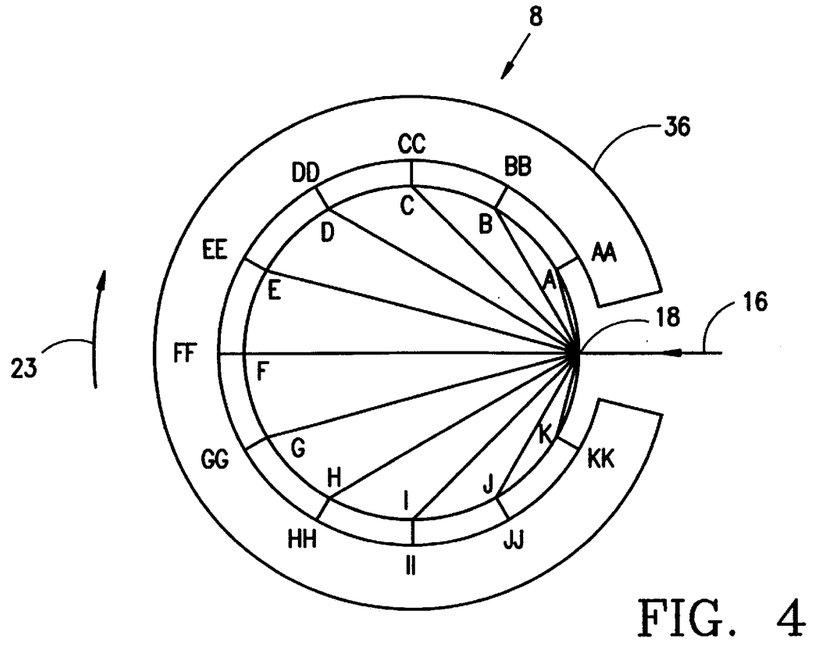
FIG. 4 is a schematic diagram of the scanning chamber of FIG. 2.

The scanning chamber 8 is represented schematically in FIG. 4. The detectors 30 are shown as AA, BB, . . . , KK, indicating their respective positions along the arc. Optical path lengths taken by the laser beam through the object are represented as chords 18-A, 18-B, . . . , 18-K. At each angular position in the orbit 23, the data collected by the detectors AA, BB, . . . , KK are generally indicated by the response curve 48 shown in FIG. 5. The signals seen by the detectors AA and KK are strongest because of the shorter chord lengths 18-A and 18-K. The signal seen by the detector FF is smaller because of its corresponding longer chord length 18-F. It is therefore seen that the signal generally decreases from detectors AA to FF and increases from detectors FF to KK.

Figure 5:
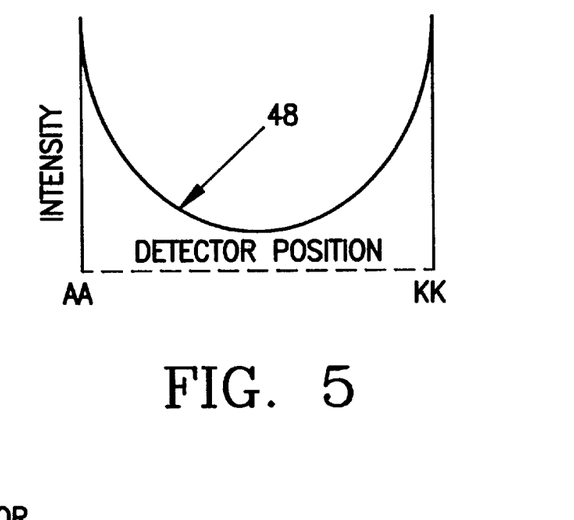
FIG. 5 is a response curve representing the data points for each of the detectors at each angular position in the orbit of the scanner.
Figure 6:
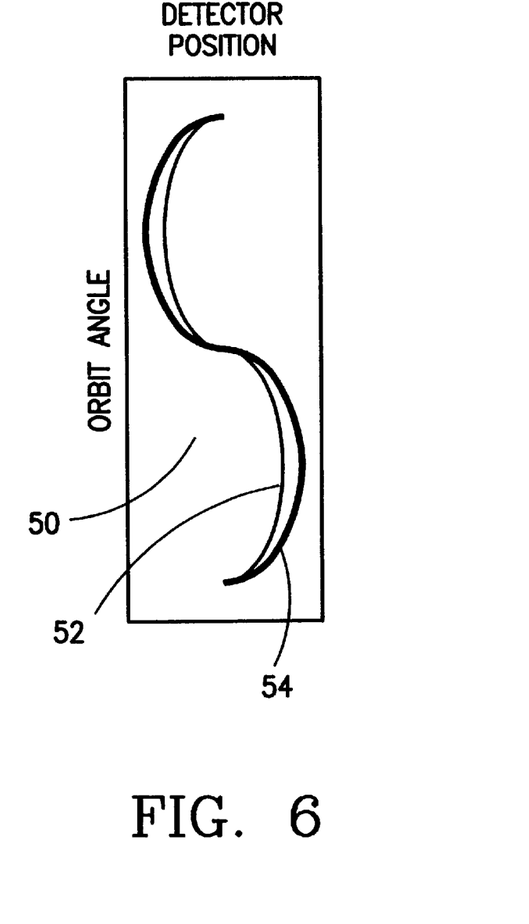
FIG. 6 is a schematic representation of a data array for each detector data for each angular position in the orbit in a complete circle around the object.

The data represented by the curve 48 and the perimeter data at each angular position of orbit are collected simultaneously, until the orbit has traversed a complete circle. The image data for each orbit position of the scanner are mapped into a matrix 50, as best shown in FIG. 6. Each row of the matrix represents values of the signals received at each respective detector location for each orbit position. An inclusion off-centered from the orbit axis within the object 14 will trace a sinusoidal curve 52 when the matrix is viewed in gray scales. Because of optical distortion, the inclusion will appear much bigger and offset from its true position, as represented by the sinusoid 54.

Envelope subtraction is performed on the fan data represented by the curve 48 to generate a fan beam matrix containing the perturbations in the measured data with respect to an exponential model. Perturbation data (projection data with perturbation) is generated by subtracting from the measured data an envelope that is based on the solution to the diffusion equation in an infinite whole space. This provides only perturbations in intensity measurements which result in changes in $\mu s'$ and $\mu a$ from their background values. Given the chord lengths from the perimeter data, an initial envelope is generated by substituting the initial values of $\mu s'=1$ and $\mu a=0.006$ into the diffusion equation, $$\Phi(r)=[1/(r*c*D(2\pi)^{3/2})][\exp-(\mu a/D)^{1/2}*r],$$

where r=chord length, c=speed of light, $D=\frac{1}{3}(\mu a+\mu s')$, $\mu s$=scattering coefficient$\approx 1.0$ mm$^{-1}$, $\mu a$=absorption coefficient$\approx 0.006$ mm$^{-1}$.

A first order linear fit of the logarithm of the model to the logarithm of the measured data is performed for each fan of data. Thus, each fan has a unique set of linear coefficients. The average of all coefficients is then used as the final coefficient to match the model data to the background unperturbed data using a first order polynomial fit to match the model envelope to the data, as follows, Data measured=[$\Phi(r)$*constant multiplier+constant offset].

The model data is then subtracted from the measured data to obtain the perturbation function.

Envelope subtraction is used to make the detectors see equal signals for a homogeneous object, in effect flattening out the response curve 48, so that any perturbations caused by an inclusion within the object, would be highlighted.

Figure 7:
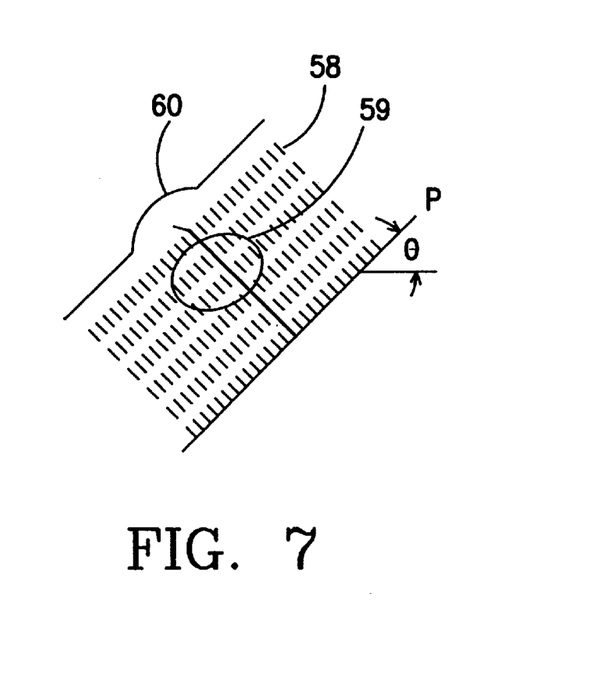
FIG. 7 is a parallel ray geometry used for backprojection reconstruction.

The image data after envelope subtraction is transformed into a standard CT geometry, using parallel ray configuration, with the P axis indicating locations of the detectors and angle $\Theta$ as the orbit position for each fan data, as best shown in FIG. 7. The transformation involves well known interpolation techniques. The perimeter information is used in the parallel ray transformation. P-$\Theta$ space is the traditional data domain for x-ray based tomography. Data in p-$\Theta$ space consists of regularly spaced samples of the object acquired along parallel rays 58, which are perpendicular to the p-axis, which is rotated some distance $\Theta$ about the origin of reconstruction space. The parallel rays pass through the object perimeter 59. The sampled data for a single angle $\Theta$ is the profile 60 of the object at that angle. Profiles from many different angles are summed during the backprojection reconstruction process to create an image of the object.

Figure 8:
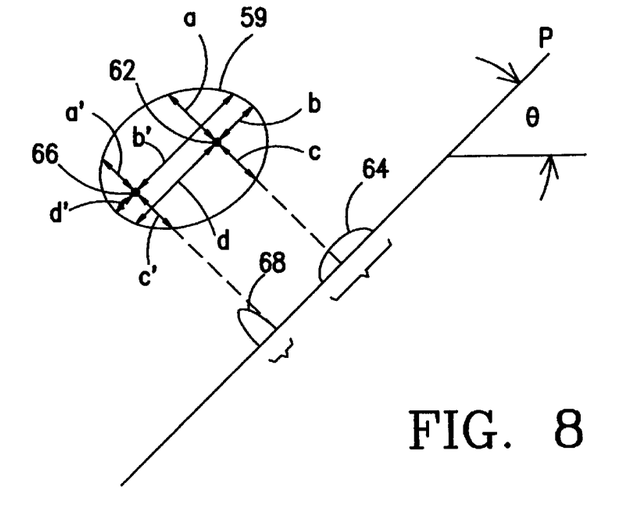
FIG. 8 shows the depth-dependent distortion of an inclusion within the object.

Fan data or projection data suffer from depth dependent blurring, geometric distortion and amplitude modulation. Referring to FIG. 8, an inclusion 62 disposed at distances a, b, c and d from the perimeter 59 has a projection data 64 that is relatively wide and short. Another inclusion 66 of the same size located at a', b', c' and d' from the perimeter has a projection data 68 that is relatively taller and narrower. The inclusion 62 appears wider from its signal profile 64 due to its being deeper into the object than the inclusion 66 which is closer to the perimeter, based on their respective abcd parameters. In general, an inclusion at the center of the object would appear bigger than one near the perimeter. The signal profiles 64 and 68 are also shown shifted, indicating geometric distortion to the reconstructed image if not corrected.

Each pixel or matrix element within the perimeter is defined by its orthogonal distances a, b, c and d. Depending on the location of the matrix element, a deblur correction factor and a distortion correction factor are applied to each pixel to generate an accurate reconstructed image.

Phantom data is acquired by scanning several phantoms that simulate breast tissues with known object size and location. A cylindrical bucket is used and filled with liquid, such as interlipid, that simulates breast tissue. A pin of known diameter is placed at a known distance from the edge of the bucket. A scan is made and the resulting reconstructed image is compared with the actual phantom. The amount of how much wider the pin appears is recorded to provide an amount of how much smaller (to deblur) the pin image will need to be made. The amount of shifting of the pin is also recorded to provide the amount of how much it will have to be shifted to its true location. The pin is then moved to a different location and another scan is made and the image size and location compared with the actual phantom. This process is repeated until enough points are plotted to obtain a curve fit. The resulting curve, a function of how much to deblur based on distance from the edge is developed and stored for use in image reconstruction. Another curve is developed from the phantom data for distortion (shifting) correction.

Several curves are developed specific to different types of breast tissues (young breast, fatty breast, etc.) characterized by their own particular set of scattering and attenuation characteristics. The phantom data is used by an off-line diffusion modeler to compute diffusion calibration data, $\mu a$ and $\mu s'$. The diffusion calibration data and perimeter data are used to compute a distortion correction factor and a matched filter deblur factor for the type of breast tissue to be scanned.

Multiple-width Gaussian functions are generated and are used in generating a convolved depth dependent array. These filters are determined empirically from phantom scans based on the maximum size of the expected objects and the inherent characteristics of the perturbation functions and are optimized for a specific blurring width. Preferably eight filters are generated, each filter designed for different depth of the pixel in the image space from the edge of the boundary of the image. Each filter is the product of the FFTs of a Gaussian function and a ramp filter. One matched filter differs from the next only in the FWHM of the Gaussian function. Each matched filter is the frequency domain product of a Gaussian function and a standard ramp filter. Each matched filter's Gaussian component has a different standard deviation; namely 0.1, 0.1, 0.15, 0.25, 0.4, 0.6, 0.85 and 1.15. Pixels close to the edge of the boundary use a ramp filter convolved with a Gaussian of width of 0.1 to enhance high frequencies. Pixels in the center are reconstructed with projection data which is filtered with a ramp filter convolved with a Gaussian of width (standard deviation) of 1.15 to cut-off high frequencies. Pixels in between the edge and the center use the intermediate filters.

The input projection at each angle Θ is convolved with the eight matched filters, generating a convolved depth data array (CDDA) table that is depth dependent and noise removed. The CDDA is used during backprojection reconstruction, which is pixel dependent selection of one of the precomputed filtered projections. In addition to deblurring, the matched filters enhance detectability in the reconstruction because they increase signal to noise ratio.

Correction to amplitude distortion is pixel dependent floating point multiplicative correction. Reconstruction uses a depth-dependent amplification factor to weight the reconstructed image. The amplification factor is empirically determined from phantom scans. Generally it is a sinusoidal function of a pixel's depth within the reconstructed image. Pixels in the center of the image have a higher amplification factor than do pixels at the edge of the image.

Figure 9:
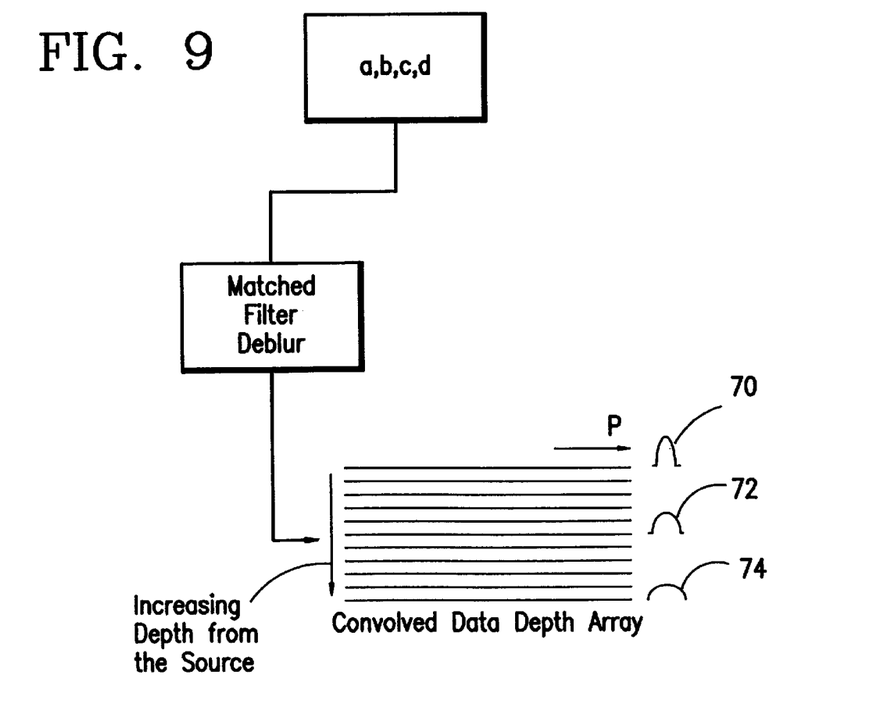
FIG. 9 is a flowchart showing the use of abcd parameters of each pixel within the perimeter of the image space to access a look-up table of filtered data.
Figure 10:
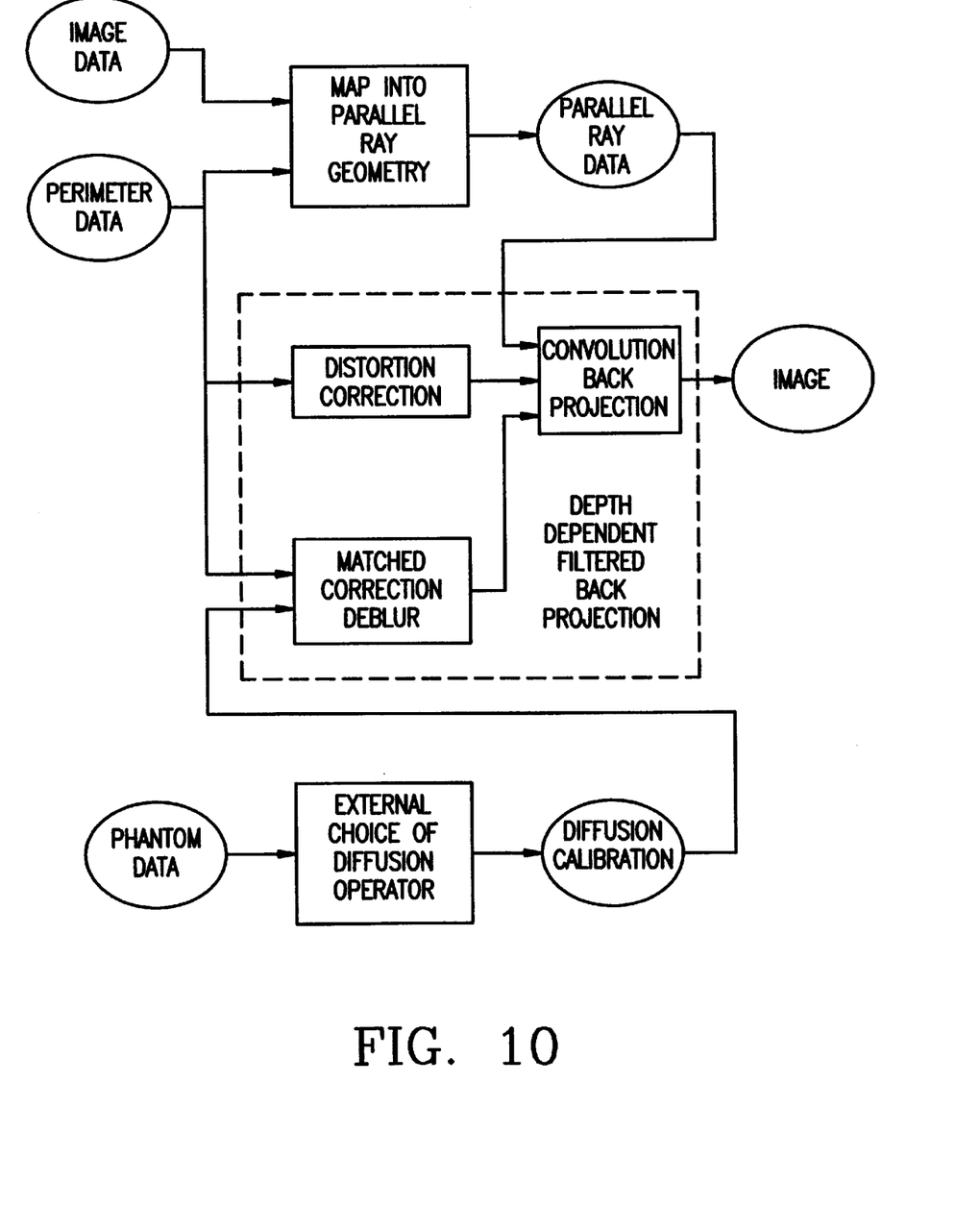
FIG. 10 is a flowchart of image reconstruction in accordance with the present invention.

Backprojection is depth-dependent matched filtering with geometric distortion correction. Each projection data is convolved with each of the eight matched filters to generate the CDDA table. For each detector reading that is backprojected, the abcd parameters of each pixel are calculated from the perimeter data, as best shown in FIG. 9. Depending on the pixel depth will dictate which one of the convolved array to use. Each pixel gets its input from one point on the projection line from a selected row of the CDDA table based on that pixel's depth, or possibly an interpolation between two rows. The width of the projection data profile at each row decreases with increasing depth from the source (laser beam), as generally indicated by the curves 70, 72 and 74.

Geometric distortion is corrected by shifting left or right on the convolved array and picking the value after shifting to use to backproject. The required geometric shift is dependent on the depth as well as the width of each pixel's position from the boundary for each projection angle and is determined empirically from phantom scans.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

We claim:

1. A method for reconstructing an image of a scanned object, comprising:
   a) collecting object data by scanning the object with a laser beam and detecting the light passing through the object;
   b) collecting perimeter data of the object during said scanning;
   c) transforming the object data to parallel ray geometry;
   d) correcting the object data using the perimeter data; and
   e) backprojecting the corrected object data in image space.

2. The method of claim 1, wherein said detecting is performed with a plurality of detectors disposed around the object.

3. The method of claim 1, wherein said collecting the object data is performed as the laser beam is moved to different locations around the object.

4. The method of claim 1, wherein said transforming to parallel geometry includes subtracting a model envelope from the object data.

5. The method of claim 4, wherein said model envelope is generated using the equation, $$\Phi(r)=[1/(r^c^D(2\pi)^{3/2})][\exp-(\mu a/D)^{1/2}*r],$$

where r=chord length,
c=speed of light,
$D=\frac{1}{3}(\mu a+\mu s')$,
$\mu s'$=scattering coefficient≈1.0 mm$^{-1}$,
$\mu a$=absorption coefficient≈0.006 mm$^{-1}$.

6. The method of claim 1, wherein said using the perimeter data includes calculating the location of each pixel from the perimeter of the object in the image plane.

7. The method of claim 6, wherein said calculating includes defining each pixel by its orthogonal distances to the perimeter of the object.

8. The method of claim 1, wherein said correcting the object data includes deblurring the object data.

9. The method of claim 8, wherein said correcting the object data includes convolving the object data with matched filters and storing the result in a table.

10. The method of claim 9, wherein said backprojecting includes picking a value from the table depending on the depth location of a pixel from the perimeter.

11. The method of claim 10, wherein:
    a) said backprojecting further includes shifting left or right within the table depending on the depth and width location of the pixel from the perimeter; and
    b) picking another value from the table.

12. The method of claim 11, wherein said backprojecting further includes applying an amplification factor to the another value depending on the depth location of the pixel from the perimeter.

13. The method of claim 8, wherein:
    a) said deblurring includes convolving the object data with matched filters and storing the result in a table; and
    b) picking a value from the table depending on the depth location of a pixel from the perimeter.

14. The method of claim 1, wherein said correcting the object data includes correcting for geometric distortion.

15. The method of claim 14, wherein:
    a) said correcting for geometric distortion includes convolving the object data with matched filters and storing the result in a table;
    b) choosing a location within the table depending on the depth location of a pixel from the perimeter; and
    c) shifting left or right within the table to pick a value depending on the width location of the pixel from the perimeter.

16. The method of claim 1, wherein said correcting the object data includes correcting for amplitude distortion.

17. The method of claim 16, wherein:
    a) said correcting for amplitude distortion includes convolving the object data with matched filters and storing the result in a table;
    b) picking a value from the table depending on the depth location of a pixel; and
    c) applying an amplification factor to the value.

18. An apparatus for imaging an object, comprising:
    a) a scanning chamber for receiving therein an object to be scanned;
    b) a source of laser beam disposed within said scanning chamber for impinging on the object, said laser beam being adapted to orbit around the object;

c) a first array of sensors disposed within said chamber, each of said first array sensors being adapted to detect light after passage through the object and thereby generate object data;

d) a second array of sensors disposed within said chamber, each of said second array sensors being adapted to detect light reflected from the surface of the object and thereby generate perimeter data for the object; and e) a computer programmed for correcting the object data using the perimeter data and backprojecting the corrected object data into an image space.

19. The apparatus of claim 18, wherein said software includes transforming the object data to parallel geometry.

20. The apparatus of claim 19, wherein said transforming includes subtracting a model envelope from the object data.

21. The apparatus of claim 20, wherein said model envelope is generated using the equation, $$\Phi(r)=[1/(r*c*D(2\pi)^{3/2})][\exp-(\mu a/D)^{1/2}*r],$$

where r=chord length, c=speed of light, $D=\frac{1}{3}(\mu a+\mu s')$, $\mu s'$=scattering coefficient$\approx 1.0$ mm$^{-1}$, $\mu a$=absorption coefficient$\approx 0.006$ mm$^{-1}$.

22. The apparatus of claim 18, wherein said correcting the object data includes calculating the location of each pixel from the perimeter of the object in the image plane.

23. The apparatus of claim 22, wherein said calculating includes defining each pixel by its orthogonal distances to the perimeter of the object.

24. The apparatus of claim 18, wherein said correcting the object data includes deblurring the object data.

25. The apparatus of claim 24, wherein:

a) said deblurring includes convolving the object data with matched filters and storing the result in a table; and b) picking a value from the table depending on the depth location of a pixel from the perimeter.

26. The apparatus of claim 18, wherein said correcting the object data includes correcting for geometric distortion.

27. The apparatus of claim 26, wherein:

a) said correcting for geometric distortion includes convolving the object data with matched filters and storing the result in a table;

b) choosing a location within the table depending on the depth location of a pixel from the perimeter; and c) shifting left or right within the table to pick a value depending on the width location of the pixel from the perimeter.

28. The apparatus of claim 18, wherein said correcting the object data includes correcting for amplitude distortion.

29. The apparatus of claim 28, wherein:

a) said correcting for amplitude distortion includes convolving the object data with matched filters and storing the result in a table;

b) picking a value from the table depending on the depth location of a pixel; and c) applying an amplification factor to the value.

30. The apparatus of claim 18, wherein said correcting the object data includes convolving the object data with matched filters and storing the result in a table.

31. The apparatus of claim 30, wherein said backprojecting the corrected data includes picking a value from the table depending on the depth location of a pixel from the perimeter.

32. The apparatus of claim 31, wherein:

a) said backprojecting the corrected data further includes shifting left or right within the table depending on the width location of the pixel; and b) picking another value from the table.

33. The apparatus of claim 32, wherein said backprojecting the corrected data further includes applying an amplification factor to the value from the table depending on the depth location of the pixel from the perimeter.

* * * * *